United States Patent [19]
Bray, Jr.

[11] Patent Number: 5,586,989
[45] Date of Patent: Dec. 24, 1996

[54] MICROSURGICAL CURETTE

[76] Inventor: Robert Bray, Jr., 17724 Camino de Yatasto, Pacific Palisades, Calif. 90272

[21] Appl. No.: 379,738

[22] Filed: Jan. 27, 1995

[51] Int. Cl.$^6$ .................................................. A61B 17/22
[52] U.S. Cl. ............................ 606/160; 606/161; 606/84
[58] Field of Search ............................ 606/160, 84, 161, 606/82, 85, 83, 167, 170, 79; 128/757, 758, 760; 30/337, 330

[56]  References Cited

U.S. PATENT DOCUMENTS

| | | | |
|---|---|---|---|
| 312,310 | 11/1990 | Michelson | D24/30 |
| 4,985,035 | 1/1991 | Torre | 606/84 |
| 5,234,452 | 8/1993 | Wang-on | 606/160 |
| 5,250,061 | 10/1993 | Michelson | 606/160 |

OTHER PUBLICATIONS

American V. Mueller The Surgical Armanetarium 1980 (p. 648).
Zimmer Catalog Supplement 1983 (pp. B245 and B246).
Tsuji et al., *Comprehensive Atlas of Lumbar Spine Surgery*, Mosby Year Book: St. Louis (1991) pp. 44–45.

*Primary Examiner*—Michael P. Buiz
*Assistant Examiner*—Kevin Truong
*Attorney, Agent, or Firm*—Christie, Parker & Hale, LLP

[57] ABSTRACT

A curette including a cylindrical handle, having a longitudinal axis, and a shaft, having a longitudinal axis. The shaft is attached to the cylindrical handle at a first end of the shaft, such that the longitudinal axis of the shaft is parallel to, but not collinear with, the longitudinal axis of the cylindrical handle. A tip is included in a second end of the shaft.

9 Claims, 1 Drawing Sheet

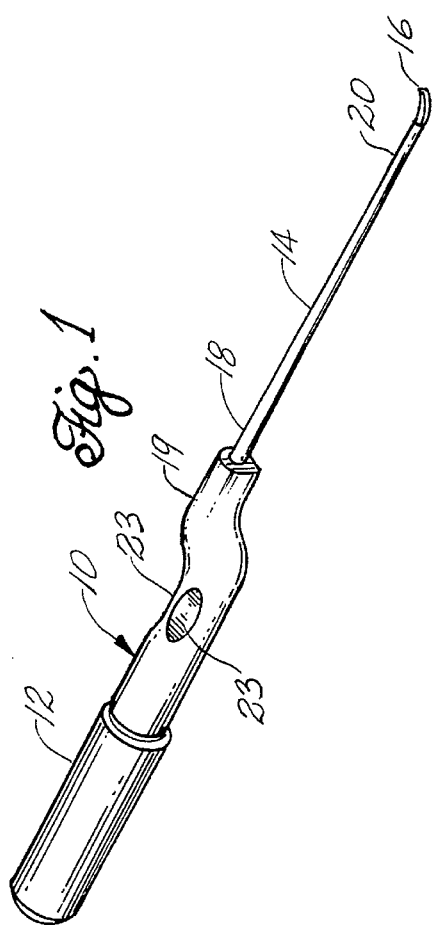
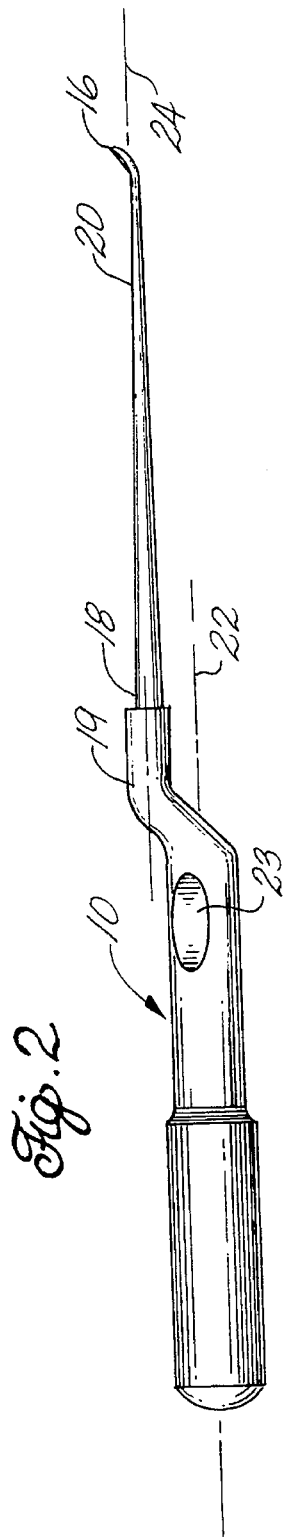
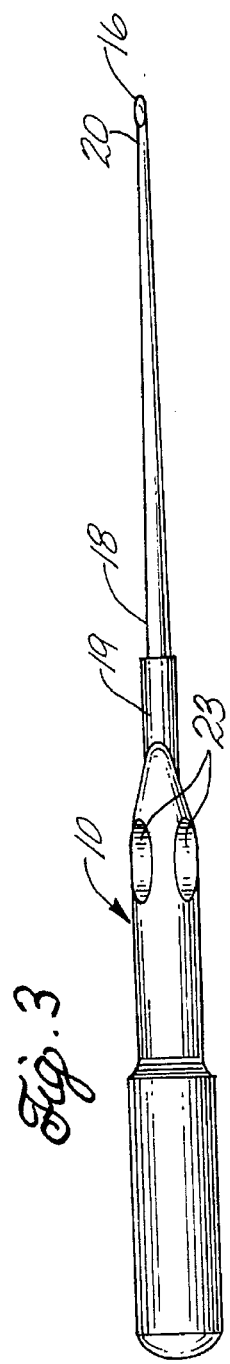

MICROSURGICAL CURETTE

FIELD OF THE INVENTION

The present invention relates to a microsurgical curette for use in spinal surgery.

BACKGROUND OF THE INVENTION

A curette is a surgical instrument with a handle, a shaft, and a cup- or spoon-shaped tip. The curette is used for scraping and scooping out bone spurs and other diseased or injured bodily tissues. In one particular application curettes are used in spinal surgery for the removal of bone spurs from vertebrae. The edge of the cup-like tip has a sharpened rim to enhance its effectiveness for scraping and cutting bone.

In use, the tip of the curette is placed into the area of tissue to be removed and scraped against the tissue. When the cup is filled the instrument is removed from the wound and the tissue within the cup is emptied. This process constitutes a "pass." The instrument is then returned to the wound, where the process is repeated until all the diseased or damaged tissue has been removed. When using conventional curettes for micro-spinal surgery, 12 to 14 passes are usually required to remove a bone spur.

A number of curettes are known in the art. One such curette is the flat-edged curette. The tip of this curette is positioned on a shaft, the longitudinal axis of which is parallel to and collinear with the longitudinal axis of a round handle. For the removal of cancellous bone with a flat-edged curette axial rotation of the curette is not sufficient. To be effective the tip must pivot around the longitudinal axis. Thus, this design is not suitable for curettage of bone or ligament in a limited space such as the spinal canal.

Another curette is the angle-edged curette. The angle-edged curette has a tip which is angled at 15° to the longitudinal axis. The longitudinal axis of the shaft is also parallel to and collinear with the longitudinal axis of the handle. The angle-edged curette is an improvement on the flat-edged design in that it does not have to be pivoted around the longitudinal axis to be effective. Rotation of the angle-edged curette around the longitudinal axis automatically provides the circular movement of the tip with a greater radius, resulting in a significantly improved performance of bone curettage and cancellous bone removal. However, in use the fingers of the user, grasping the handle, often obscure the view of the tip, making delicate procedures difficult and potentially dangerous.

Another design is that described in U.S. Pat. No. Des. 312,310. In this curette design the shaft is neither collinear nor parallel with the handle, but instead is placed on one side of a square cross-sectional handle. The shaft is angled toward the axis of the handle which places the tip in a position which is collinear with the axis of the handle. However, in this design the user's fingers also obscure the view of the tip in the field of the microscope used for the microsurgery. Accurate placement of the tip is difficult when the view of the tip of the curette is obscured by the fingers of the user during use. Moreover, the square cross-sectional handle makes rotation of the curette difficult. Another feature of this design is that the tip of the curette is angled. While this angle makes scraping of tissue easier, the tip is susceptible to breakage allowing this small piece of the curette to drop into the site of the surgery. The tip must be recovered before completion of the surgical procedure and "hunting" for the broken tip increases the possibility of unintentional damage to tissue at the site of the surgery.

Another curette design is a ring curette. This type of curette is one in which the cup of the tip does not have a bottom and the tip is in the form of a ring. This type of curette is used for soft tissue removal and is not suitable for the removal of bone.

There is a need for a curette for use in micro-spinal surgery which allows the user to place the device to accurately and to "set" the edge of the curette to effectively remove the desired tissue. It is also desirable that the tip of the curette is sufficiently strong to withstand the forces placed on it during normal use without breaking. It is also desirable that only are a few passes are required to remove bone spurs.

SUMMARY OF THE INVENTION

The present invention is directed to a curette for use in spinal surgery. The curette comprises a cylindrical handle and a shaft, each having a longitudinal axis. The shaft is attached to the cylindrical handle at a first end of the shaft, such that the longitudinal axis of the shaft is parallel, but not collinear with, the longitudinal axis of the cylindrical handle. A tip is included in a second end of the shaft.

BRIEF DESCRIPTION OF THE DRAWINGS

Features, aspects, and advantages of the present invention will be more fully understood when considered with respect to the following detailed description, appended claims, and accompanying drawings, where:

FIG. 1 is a perspective view of a curette of the present invention;

FIG. 2 is a schematic side view of a curette of the present invention; and

FIG. 3 is a schematic top view of a curette of the present invention.

DETAILED DESCRIPTION

The present invention is directed to a curette for use in surgery on vertebrae and the spinal column.

The curette 10 of the present invention is illustrated in FIGS. 1 to 3. The curette comprises a handle 12, a shaft 14 and a tip 16.

The handle, at a first end, is a cylindrical shaped member (see FIG. 1) having a longitudinal axis 22 through its center (see FIG. 2). At a second end of the handle, adjacent to the first end, are finger grips 23 are indented into the generally cylindrical shaped handle. The finger grips allow the curette to be rocked to allow the tip to be "set." Setting of the tip means that the tip is held at an angle to the bone to be cut such that the blade of the tip, described below, is angled to cut into the bone. The cylindrical shape of the handle allows the curette to be rocked or partially rotated around the longitudinal axis of the handle in a smooth and controlled manner, when the curette is in use.

Attached to one end of the handle is a shaft 14. The shaft has a generally circular cross-section, which has a larger diameter at one end, a first end 18, where the shaft attaches to the handle, and tapers to a smaller diameter at its other end, a second end, 20. The shaft's diameter, at its largest point, is smaller than the diameter of the handle. The shaft is preferably attached to the handle at a point on the perimeter of the cylindrical handle. The shaft is attached to the handle such that longitudinal axis 24 of the shaft is generally parallel to the longitudinal axis of the handle (see FIG. 2). However, since the shaft is attached to the perimeter of the handle, the longitudinal axis of the shaft is not collinear with the longitudinal axis of the handle.

In one embodiment of the present invention a mechanism for attaching the shaft to the handle comprises an arm 19 extending from the circumferential perimeter and from one end, of the cylindrical handle. The arm extends away from the axis 22 of the handle and then bends to provide a point of attachment of the shaft with its axis parallel to the axis of the handle. In an alternative embodiment of the present invention a mechanism for attaching the shaft to the handle comprises an arm (not shown) extending from the center of the cylindrical handle. The arm bends and extends away from the axis of the handle and then bends to provide a point of attachment of the shaft with its axis parallel to the axis of the handle.

In one embodiment of the invention the handle and the shaft/tip section are made as separate units which are joined for use as shown in FIGS. 1 to 3. Curettes made as separate units have the advantage of interchanging different size tips, and different length shafts, without the necessity of purchasing different handles thus saving on the cost of the curettes. In this detachable embodiment of the invention the shaft/tip section can be attached to the handle using a screw mount, a bayonet mount, by inserting the shaft into a socket in the handle and securing the shaft in place with screws through the handle into the shaft or by other suitable means of connection. In one embodiment of the present invention the shaft and tip of the curette are unitarily molded to the handle. This unitary molding allows for easy cleaning and sterilization of the curette.

Included in end 20 of the shaft is a tip 16. The tip is an elongated cup shaped member which is molded into the end of the shaft. In one embodiment, the tip is set at an angle to the longitudinal axis of the shaft, of about 15° in an upward, away from the longitudinal axis of the handle, direction. However, other angles may be chosen as required. The edges of the tip are sharpened to create a cutting surface. The angled tip allows the surgeon to remove tissue by setting the tip and scraping against the tissue, i.e., parallel to the longitudinal axis of the handle, scraping motion and by axial rotation of the curette.

The attachment of the shaft to the handle in an orientation that is generally parallel to the longitudinal axis of the handle allows the surgeon to set the cutting edge of the curette and accurately predict the position of the tip of the curette once it has been set. This prevents damage to tissue surrounding the site of the surgery that can occur when the tip of the curette is set and accidentally brushes against such tissue. The elongated cup shaped member provides a larger cutting surface than rounded cups of conventional curettes. The larger cutting edge results in only about 1 to 2 passes being required to remove bone spurs.

The tip of the curette of the present invention is molded into the shaft, i.e. is "cut" into the shaft, rather than, as in the conventional curettes, attached to the tapered shaft. Inclusion of the tip in the shaft results in a stronger tip-shaft connection which can withstand much greater forces than conventional curettes. Conventional curettes frequently suffer stress fractures at the union of the tip and the shaft. Since the structure of the present invention is much stronger than conventional curette designs the tips of the present invention can be made much thinner making microsurgery safer and more easily performed.

The arrangement of the curette, with the shaft parallel to, but not collinear with the handle allows the surgeon to view the tip of the curette while the curette is being used. This allows the surgeon to accurately place the tip of the curette at the required site. It also allows the surgeon to remove tissue as needed while visually monitoring the amount of tissue which has been removed and to ensure that only diseased or damaged tissue is removed. The visual observations aids the surgeon in avoiding damage to other healthy tissue in the region of the site of the surgery. Also when the curette of the present invention is in use the fingers of the surgeon are placed in a position which is collinear with the longitudinal axis of the shaft. Therefore, when the curette is rocked to set the tip, the tip rotates in a small arc, the position of which can be easily predicted by the surgeon.

The curette of the present invention is fabricated from stainless steel or other materials suitable for use in surgical procedures.

In use the curette is inserted into the area of the tissue to be removed. The surgeon can place the tip accurately by visually observing, typically through a microscope, the placement of the tip without having to move his or her fingers from their position on the handle and without having to move the tip of the curette to a position where it can be observed but not where it is to be used. After placement in the region to be treated the tip is set to place the cutting edge in the desired position against the bone and tissue is removed by scraping the tip across the surface, i.e., in a direction parallel to the longitudinal axis of the handle. Throughout the placement of the tip the surgeon can observe the tip in relation to vital structures in the body of the patient. The observation does not require moving the surgeon's fingers from the handle or moving the curette into a different position so that an observation can be made. As a result of these advantages of the curette of the present invention micro-spinal surgery can be performed with a greater degree of accuracy in the placement of the tip of the curette and, therefore, with a greater degree of safety.

One embodiment of the present invention is described in detail above and is for illustration purposes. Variations will be apparent to those skilled in the art. Therefore, the present invention is not intended to be limited to the working embodiment described above. Rather, the scope of the invention is defined in the following claims.

What is claimed is:

1. A curette comprising:

a cylindrical handle having a longitudinal axis;

a shaft, having a longitudinal axis;

means or attaching a first end of the shaft to the cylindrical handle, such that the longitudinal axis of the shaft is parallel to, but not collinear with, the longitudinal axis of the cylindrical handle; and a tip included in a second end of the shaft.

2. A curette as recited in claim 1 wherein the shaft is attached to the circumferential perimeter of the cylindrical handle.

3. A curette as recited in claim 1 wherein the tip is angled, with respect to the longitudinal axis of the shaft, away from the longitudinal axis of the handle.

4. A curette as recited in claim 1 wherein the tip is an elongated cup.

5. A curette as recited in claim 1 wherein the means for attaching the shaft to the cylindrical handle comprises an arm extending from the circumferential perimeter of the cylindrical handle.

6. A curette as recited in claim 1 wherein the shaft is unitarily molded with the handle.

7. A curette comprising:

a cylindrical handle having a longitudinal axis;

a shaft comprising:
- a first end, wherein the first end of the shaft is attached to the handle;
- a longitudinal axis, wherein the longitudinal axis of the shaft is parallel to, but not collinear with, the longitudinal axis of the handle; and
- a second end; and a tip included in the second end of the shaft wherein the tip is angled, with respect to the longitudinal axis of the shaft, away from the longitudinal axis of the handle.

8. A curette as recited in claim 6 wherein the tip is an elongated cup.

9. A curette comprising:

a cylindrical handle having a first longitudinal axis;

a shaft having a second longitudinal axis;

means for removably attaching a first end of the shaft to the cylindrical handle, such that the second longitudinal axis of the shaft is parallel to, but not collinear with, the first longitudinal axis of the cylindrical handle, said means including an arm extending from the circumferential perimeter of the cylindrical handle; and an elongated cup molded into the second end of the shaft, wherein the elongated cup is angled, with respect to the second longitudinal axis of the shaft, away from the first longitudinal axis of the cylindrical handle.

* * * * *